US 7,888,932 B2

(12) United States Patent
McKnight et al.

(10) Patent No.: US 7,888,932 B2
(45) Date of Patent: Feb. 15, 2011

(54) SURFACE FLAW DETECTION SYSTEM TO FACILITATE NONDESTRUCTIVE INSPECTION OF A COMPONENT AND METHODS OF ASSEMBLING THE SAME

(75) Inventors: William Stewart McKnight, Hamilton, OH (US); Ui Suh, Cincinnati, OH (US); Yuri Plotnikov, Niskayuna, NY (US); Changting Wang, Niskayuna, NY (US); Ralph Gerald Isaacs, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 273 days.

(21) Appl. No.: 11/935,118

(22) Filed: Nov. 5, 2007

(65) Prior Publication Data

US 2009/0115410 A1    May 7, 2009

(51) Int. Cl.
*G01N 27/82* (2006.01)
(52) U.S. Cl. ................................. 324/242; 324/240
(58) Field of Classification Search ........... 324/237, 324/238, 240, 242
See application file for complete search history.

(56) References Cited

U.S. PATENT DOCUMENTS

| | | | |
|---|---|---|---|
| 4,310,821 A | 1/1982 | Frances | |
| 4,706,020 A | 11/1987 | Viertl et al. | |
| 5,006,800 A | 4/1991 | Hedengren et al. | |
| 5,182,513 A | 1/1993 | Young et al. | |
| 5,237,271 A | 8/1993 | Hedengren | |
| 5,262,722 A | 11/1993 | Hedengren et al. | |
| 5,278,498 A | 1/1994 | Vernon et al. | |
| 5,315,234 A | 5/1994 | Sutton, Jr. et al. | |
| 5,371,461 A | 12/1994 | Hedengren | |
| 5,371,462 A | 12/1994 | Hedengren et al. | |
| 5,389,876 A | 2/1995 | Hedengren et al. | |
| 5,418,457 A | 5/1995 | Hedengren et al. | |
| 5,442,286 A | 8/1995 | Sutton, Jr. et al. | |
| 5,659,248 A | 8/1997 | Hedengren et al. | |
| 5,801,532 A | 9/1998 | Patton et al. | |

(Continued)

FOREIGN PATENT DOCUMENTS

EP      0512796 A2    11/1992

(Continued)

OTHER PUBLICATIONS

Ditchburn, R.J., et al.; Planar Rectangular Spiral Coils in Eddy-Current Non-Destructive Inspection; NDT&E International; pp. 690-700; vol. 38, Issue 8; Dec. 2005.

(Continued)

*Primary Examiner*—Patrick J Assouad
*Assistant Examiner*—David M. Schindler
(74) *Attorney, Agent, or Firm*—William Scott Andes, Esq.; Armstrong Teasdale LLP

(57) ABSTRACT

A method of assembling an eddy current array probe to facilitate nondestructive testing of a sample is provided. The method includes positioning a plurality of differential side mount coils at least partially within a flexible material. The method also includes coupling the flexible material within a tip portion of the eddy current array probe, such that the flexible material has a contour that substantially conforms to a portion of a surface of the sample to be tested.

11 Claims, 13 Drawing Sheets

U.S. PATENT DOCUMENTS

| | | | |
|---|---|---|---|
| 5,841,277 A | 11/1998 | Hedengren et al. | |
| 5,903,147 A | 5/1999 | Granger, Jr. et al. | |
| 5,966,011 A | 10/1999 | Goldfine et al. | |
| 6,150,809 A | 11/2000 | Tiernan et al. | |
| 6,252,393 B1 | 6/2001 | Hedengren | |
| 6,452,384 B1* | 9/2002 | Becker et al. | 324/240 |
| 6,504,363 B1 | 1/2003 | Dogaru et al. | |
| 6,608,478 B1 | 8/2003 | Dziech et al. | |
| 6,693,425 B2 | 2/2004 | Wache | |
| 6,707,297 B2 | 3/2004 | Nath et al. | |
| 6,720,775 B2 | 4/2004 | Plotnikov et al. | |
| 6,727,691 B2 | 4/2004 | Goldfine et al. | |
| 6,784,662 B2 | 8/2004 | Schlicker et al. | |
| 6,812,697 B2 | 11/2004 | McKnight et al. | |
| 6,822,443 B1 | 11/2004 | Dogaru | |
| 6,888,346 B2 | 5/2005 | Wincheski et al. | |
| 6,888,347 B2 | 5/2005 | Batzinger et al. | |
| 6,911,826 B2 | 6/2005 | Plotnikov et al. | |
| 6,933,717 B1 | 8/2005 | Dogaru et al. | |
| 6,992,482 B2 | 1/2006 | Shay et al. | |
| 7,015,690 B2 | 3/2006 | Wang et al. | |
| 7,049,811 B2 | 5/2006 | Schlicker et al. | |
| 7,095,224 B2 | 8/2006 | Goldfine et al. | |
| 7,106,055 B2 | 9/2006 | Goldfine et al. | |
| 7,161,351 B2 | 1/2007 | Goldfine et al. | |
| 7,188,532 B2 | 3/2007 | Goldfine et al. | |
| 2005/0140366 A1* | 6/2005 | Bar et al. | 324/239 |
| 2005/0264284 A1* | 12/2005 | Wang et al. | 324/240 |
| 2006/0017434 A1 | 1/2006 | Tenley et al. | |
| 2006/0023961 A1 | 2/2006 | Suh et al. | |
| 2006/0109001 A1* | 5/2006 | Suh et al. | 324/232 |
| 2006/0170420 A1* | 8/2006 | Nishimizu et al. | 324/239 |
| 2006/0290349 A1 | 12/2006 | Na et al. | |

FOREIGN PATENT DOCUMENTS

EP     1202053 A1     5/2002

OTHER PUBLICATIONS

A European Search Report from the European Patent Office, dated Oct. 28, 2009, for copending European patent application No. EP08166997 (6 pages).

* cited by examiner

SURFACE FLAW DETECTION SYSTEM TO FACILITATE NONDESTRUCTIVE INSPECTION OF A COMPONENT AND METHODS OF ASSEMBLING THE SAME

BACKGROUND OF THE INVENTION

This invention relates generally to nondestructive testing, and more particularly to using an eddy current probe and methods of assembling the same.

Eddy current (EC) inspection devices are used to detect abnormal indications in a component being tested such as, but not limited to, gas turbine engine components. For example, known EC inspection devices may be used to detect cracks, pings, dings, raised material, and/or other surface imperfections on a surface of the component, and/or to evaluate material properties of the component including the conductivity, density, and/or degrees of heat treatment of the component.

During operation, known EC devices measure the interaction between an electromagnetic field generated by the EC device and the component being tested. For example, at least some known EC devices include a probe coil that generates a magnetic field. When the coil is positioned adjacent to a conductive component, an eddy current is generated on the surface of the component. A flaw on and/or near the surface of the component disrupts the eddy current field causing a secondary field to be produced that is received by the eddy current probe coil or by a sensor coil in the eddy current probe. The altered secondary magnetic field is converted to an electrical signal that may be recorded, for example, on a strip chart recorder.

In use, a substantially constant pressure is applied to the EC probe as the coil moves along the surface of the component being tested. The constant pressure facilitates maintaining an integrity of the signal generated by the EC probe. However, when the EC probe is not oriented substantially perpendicular to the surface of the component being tested, a "lift-off effect" may be created.

To facilitate reducing lift-off effects, at least one known EC probe includes a dual-coil probe, e.g. a differential probe, that includes a pair of coils with an opposite polarity. Each coil in the dual-coil probe generates an electrical signal when the probe contacts a surface of the component being tested. More specifically, when the dual coil probe passes over a smooth surface of the component being tested, the signals cancel each other. However, when the dual coil probe passes over a local physical abnormality on the surface, the probe generates a signal that is proportional to the size, depth, etc., of the physical abnormality.

FIG. 1 is a front view of an exemplary known eddy current (EC) probe 500. Eddy current probe 500 includes two differential coils coupled to a solid surface of eddy current probe 500. FIG. 2 is a top view of eddy current probe 500 shown in FIG. 1. FIG. 3 is a front view of eddy current probe 500, and illustrates the lift-off effect in an indexing direction. Eddy current probe 500 is unable to conform to the surface of the article being tested. FIG. 4 is a front view of eddy current probe 500 and illustrates the lift-off effect in a scan direction. Known differential probes may only be tiltable up to approximately 2° before the EC signal deteriorates.

As shown in FIG. 1, when a non-continuous component surface feature is inspected, such as a feature on a rotating part, known differential probes may have difficulty testing sharp curvatures, in such areas as corners and cusps. During operation, when such probes encounter a corner or cusp, the differential probe device may become skewed to the surface of the component, such that a resulting lift-off effect may cause a loss of usable data. Accordingly, known EC devices may be less effective in generating an accurate response when the EC device is used to detect conditions on a component having complex geometries, and/or a component having irregular conditions, such as may be prevalent in components including sharp indexing or objects that extend into the path of the probe such that the probe cannot consistently remain normal to the scan surface. Known EC devices include multiple EC probes oriented in an array, such that a larger area of a surface is tested at once. However, arrays of this type can increase the lift-off effect on non linear surfaces.

BRIEF DESCRIPTION OF THE INVENTION

In one aspect, a method of assembling an eddy current array probe to facilitate nondestructive testing of a sample is described. The method includes positioning a plurality of differential side mount coils at least partially within a flexible material. The method also includes coupling the flexible material within a tip portion of the eddy current array probe, such that the flexible material has a contour that substantially conforms to a portion of a surface of the sample to be tested.

In another aspect, an eddy current testing device is described. The eddy current testing device includes an eddy current array probe assembly comprising a tip portion. The eddy current testing device also includes a plurality of differential side mount coils positioned at least partially within the tip portion of the eddy current array probe, the plurality of differential side mount coils flexibly coupled together to form an array of coils.

In yet another aspect, a surface flaw detection system to facilitate nondestructive inspection of a component is described. The system includes a control system and at least one eddy current array probe communicatively coupled to the control system. The eddy current array probe includes a compressible assembly coupled to the eddy current array probe, the compressible assembly configured to substantially conform to a portion of a surface being tested when forced against the portion of the surface being tested. The eddy current array probe also includes a plurality of differential side mount coils oriented in an array, the array positioned at least partially within the compressible assembly.

DETAILED DESCRIPTION OF THE INVENTION

Figure 5:
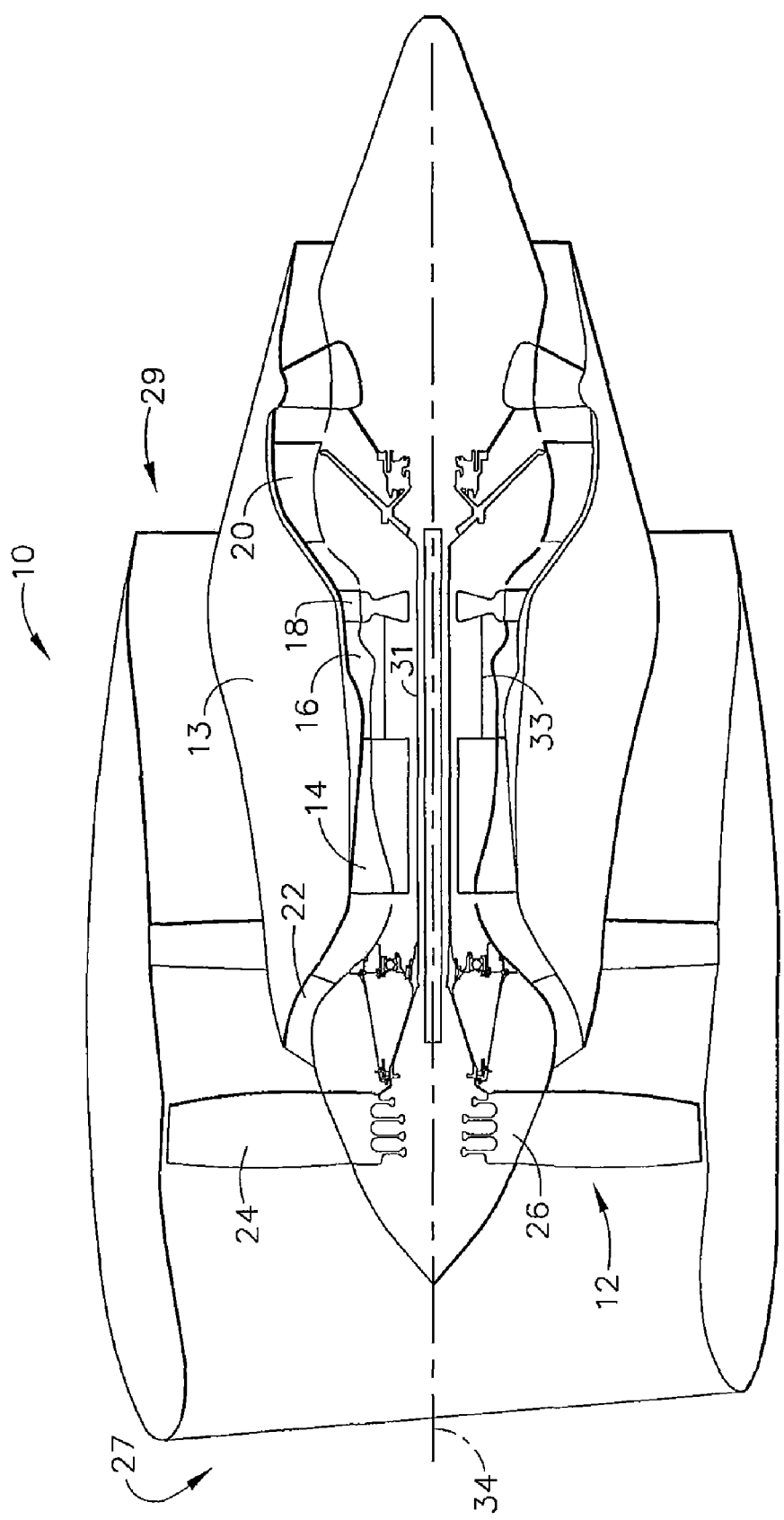
FIG. 5 is a schematic illustration of an exemplary gas turbine engine.

FIG. 5 is a schematic illustration of a gas turbine engine 10 including a fan assembly 12 and a core engine 13 including a high pressure compressor 14, and a combustor 16. Engine 10 also includes a high pressure turbine 18, a low pressure turbine 20, and a booster 22. Fan assembly 12 includes an array of fan blades 24 extending radially outward from a rotor disc 26. Engine 10 has an intake side 27 and an exhaust side 29. In one embodiment, the gas turbine engine is a GE90 available from General Electric Company, Cincinnati, Ohio. Fan assembly 12 and turbine 20 are coupled by a first rotor shaft 31, and compressor 14 and turbine 18 are coupled by a second rotor shaft 33.

Figure 1:
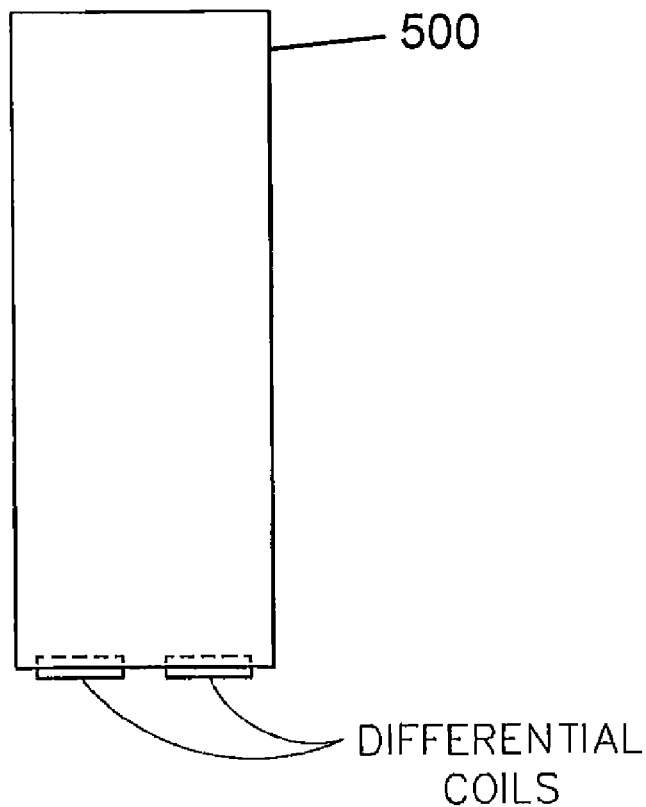
FIG. 1 is a front view of a known eddy current probe.

During operation, air flows axially through fan assembly 12, in a direction that is substantially parallel to a central axis 34 extending through engine 10, and compressed air is supplied to high pressure compressor 14. The highly compressed air is delivered to combustor 16. Airflow (not shown in FIG. 1) from combustor 16 drives turbines 18 and 20, and turbine 20 drives fan assembly 12 by way of shaft 31.

Figure 6:
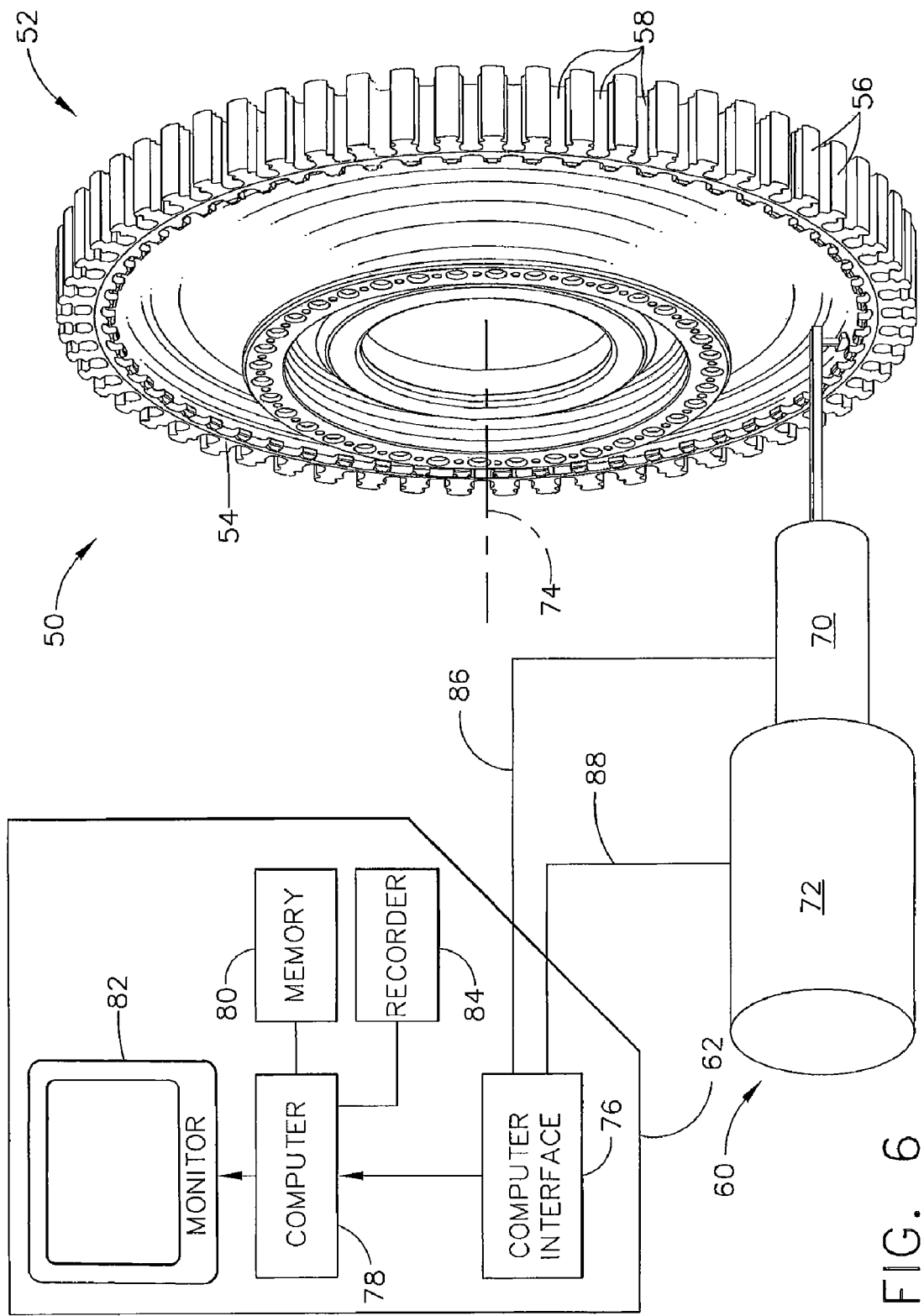
FIG. 6 is a schematic diagram of an exemplary eddy current surface flaw detection system that can be used to inspect a component.

FIG. 6 is a schematic diagram of an exemplary eddy current surface flaw detection system 50 that can be used to inspect a component 52 such as, but not limited to, a gas turbine engine disk 54 which may be used with gas turbine engine 10 (shown in FIG. 5). In the exemplary embodiment, disk 54 includes a plurality of posts 56 and a plurality of circumferentially spaced dovetail slots 58 defined between adjacent pairs of posts 56.

Although the methods and apparatus herein are described with respect to posts 56 and dovetail slots 58, it should be appreciated that the methods and apparatus can be applied to a wide variety of components. For example, component 52 may have any operable shape, size, and configuration. Examples of components may include, but are not limited to, components of gas turbine engines such as seals, flanges, turbine blades, turbine vanes, and/or flanges. The component may be fabricated of any base material such as, but not limited to, nickel-base alloys, cobalt-base alloys, titanium-base alloys, iron-base alloys, and/or aluminum-base alloys. More specifically, although the methods and apparatus herein are described with respect to turbine engine parts, it should be appreciated that the methods and apparatus can be applied to, or used to inspect, a wide variety of components used within a steam turbine, a nuclear power plant, an automotive engine, or any other mechanical components.

In the exemplary embodiment, detection system 50 includes a probe assembly 60 and a data acquisition/control system 62. Probe assembly 60 includes an eddy current coil/probe 70 and a probe manipulator 72. Eddy current probe 70 and probe manipulator 72 are each electrically coupled to data acquisition/control system 62 such that control/data information can be transmitted to/from eddy current probe 70/probe manipulator 72 and data acquisition/control system 62. In an alternative embodiment, system 50 also includes a turntable (not shown) configured to rotate component 52 about a central axis 74 during the inspection procedure.

Data acquisition/control system 62 includes a computer interface 76, a computer 78, such as a personal computer with a memory 80, and a monitor 82. Computer 78 executes instructions stored in firmware (not shown). Computer 78 is programmed to perform functions described herein, and as used herein, the term "computer" is not limited to just those integrated circuits referred to in the art as computers, but rather broadly refers to computers, processors, microcontrollers, microcomputers, programmable logic controllers, application specific integrated circuits, and other programmable circuits, and these terms are used interchangeably herein.

Memory 80 is intended to represent one or more volatile and/or nonvolatile storage facilities that shall be familiar to those skilled in the art. Examples of such storage facilities often used with computer 78 include, but are not limited to, solid state memory (e.g., random access memory (RAM), read-only memory (ROM), and flash memory), magnetic storage devices (e.g., floppy disks and hard disks), and/or optical storage devices (e.g., CD-ROM, CD-RW, and DVD). Memory 80 may be internal to or external to computer 78. Data acquisition/control system 62 also includes a recording device 84 such as, but not limited to, a strip chart recorder, a C-scan, and an electronic recorder that is electrically coupled to either computer 78 and/or eddy current probe 70.

In use, a component 52, such as disk 54, is secured in position during inspection. Eddy current probe 70 is coupled to probe manipulator 72 to position probe 70. Manipulator 72 positions probe 70 to facilitate an inspection of substantially all of the interior of each dovetail slot 58 being inspected. In the exemplary embodiment, probe manipulator 72 is a six-axis manipulator. Eddy current probe 70 is electrically coupled to data acquisition/control system 62 by a data link 86. Eddy current probe 70 generates electrical signals in response to the eddy currents induced within the surface of dovetail slots 58 during scanning by probe 70. Electrical signals generated by probe 70 are received by data acquisition/control system 62 via a data communications link 86 and are either stored in memory 80 or recorder 84. Computer 78 is also coupled to probe manipulator 72 by a communications link 88 to facilitate controlling the scanning of dovetail slots 58. A keyboard (not shown in FIG. 6) is electrically coupled to computer 78 to facilitate operator control of the inspection of disk 54. In the exemplary embodiment, a printer (not shown in FIG. 6) may be provided to generate hard copies of the images generated by computer 78.

Figure 7:
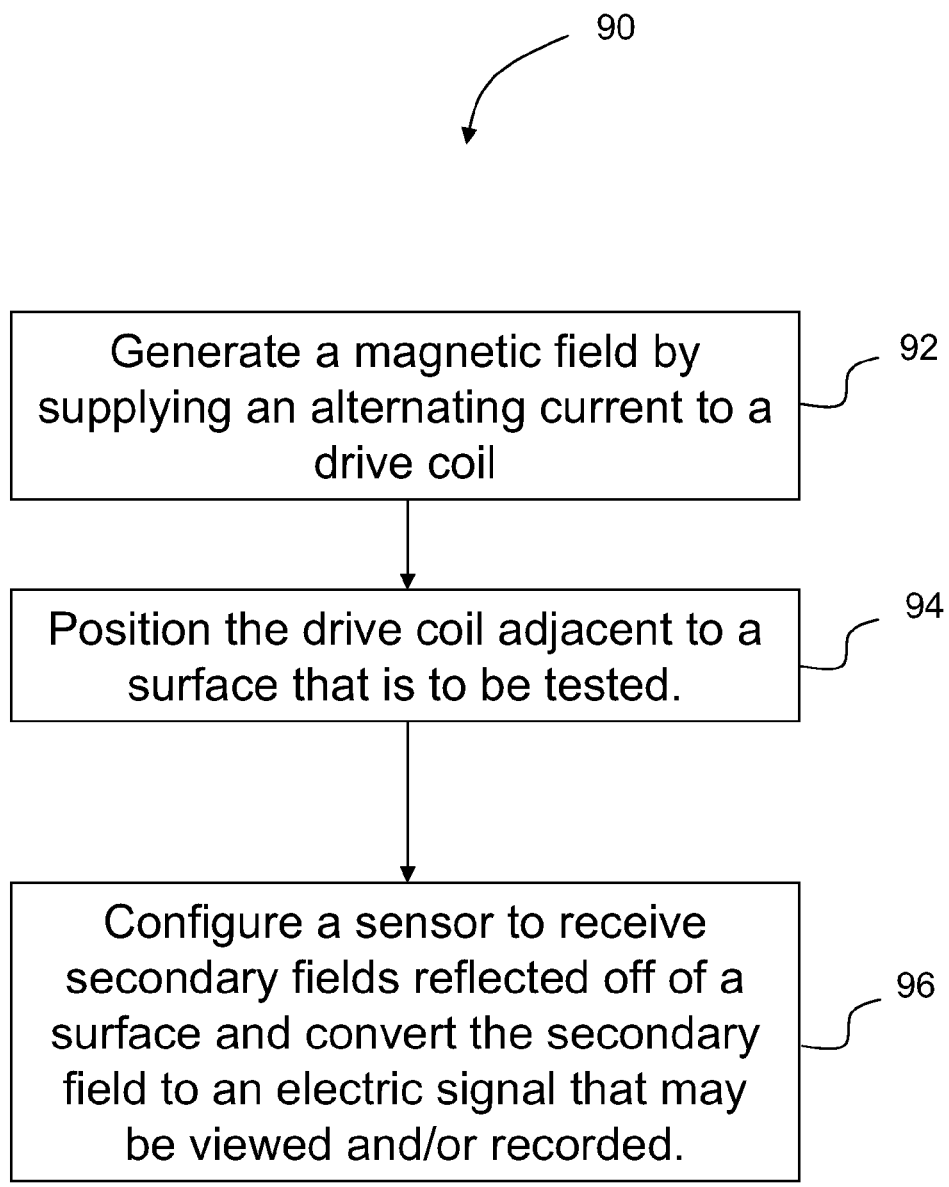
FIG. 7 is a flow chart illustrating an exemplary method for performing an eddy current inspection using the system shown in FIG. 6.

FIG. 7 is a flow chart illustrating an exemplary method 90 for performing an eddy current inspection. The method 90 includes generating 92 magnetic fields about a plurality of drive coils. Generating 92 may include, but is not limited to only supplying an alternating current to a drive coil. Method 90 also includes positioning 94 the drive coils adjacent to a surface that is to be tested. In the exemplary embodiment, positioning 94 includes orienting the drive coils substantially parallel to the surface to be tested. Such an orientation of the drive coils causes the magnetic fields generated by the drive coils to be oriented substantially normal to the surface being tested.

The method 90 also includes configuring 96 sensors to receive secondary fields. Secondary fields of interest are received at the sensors after the magnetic fields generated by the drive coils are reflected off a surface flaw on or in the surface being tested. Configuring 96 may include configuring the sensors to convert the reflected secondary fields into electric signals that may be viewed and/or recorded.

Figure 8:
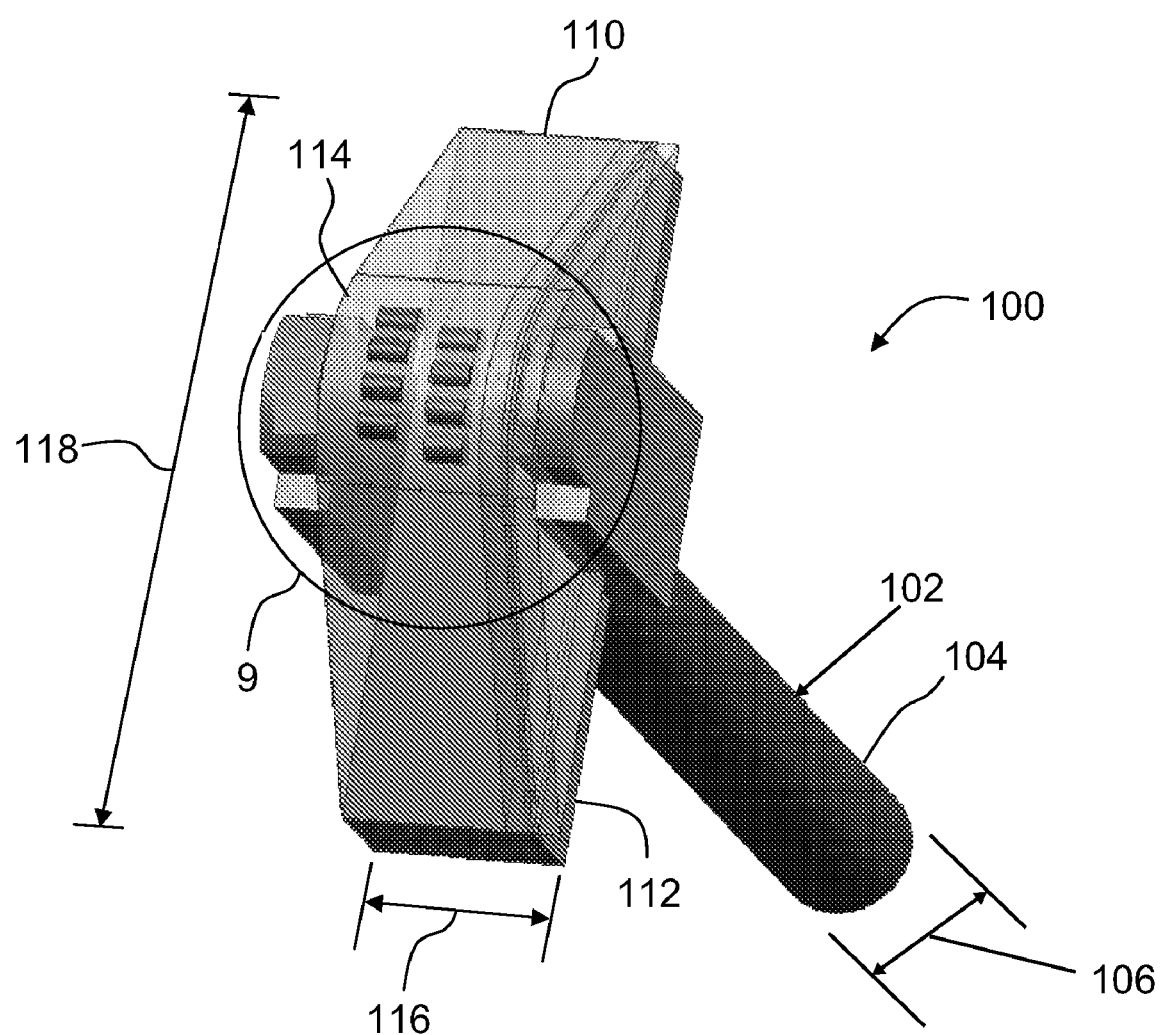
FIG. 8 is a perspective view of an exemplary eddy current array probe that may be used with an eddy current surface flaw detection system shown in FIG. 6.

FIG. 8 is a perspective view of an exemplary eddy current array probe 100 that may be used with eddy current surface flaw detection system 50 (shown in FIG. 6). In the exemplary embodiment, eddy current array probe 100 has a body portion 102 that includes an outer surface 104 and a diameter 106. In the exemplary embodiment, body portion 102 is substantially cylindrically shaped. Eddy current array probe 100 also includes a tip portion 110 that is coupled to body portion 102. Alternatively, in another exemplary embodiment, body portion 102 and tip portion 110 are integrally formed together such that body portion 102 and tip portion 110 form a unitary eddy current array probe 100.

Tip portion 110 includes an end 112 and an outer tip 114. Tip portion 110 has a width 116 and a length 118 that is longer than width 116. In the exemplary embodiment, tip portion 110 is contoured, forming an apex at outer tip 114, while width 116 remains constant.

Figure 9:
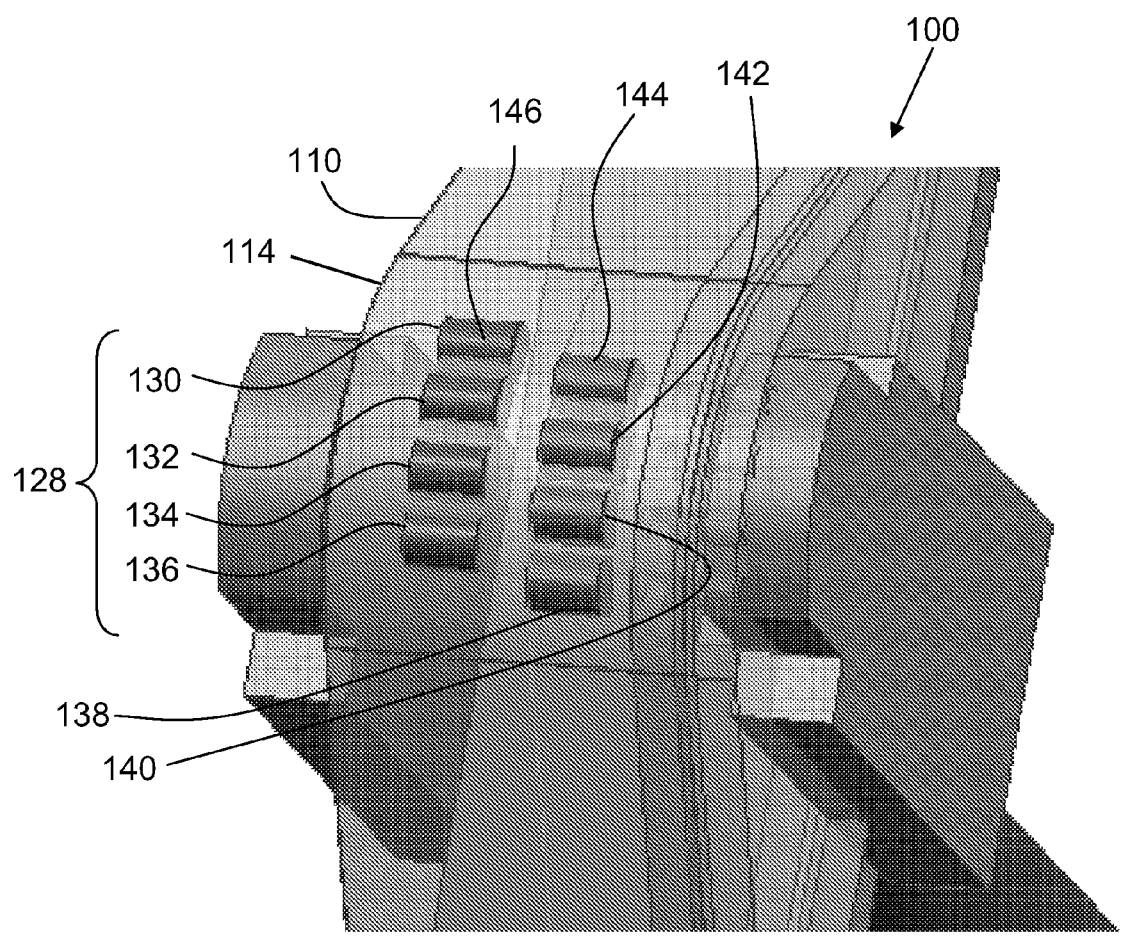
FIG. 9 is an enlarged perspective view of a portion of an eddy current array probe shown in FIG. 8 and taken along area 9 (shown in FIG. 8)

FIG. 9 is a perspective view of a portion of eddy current array probe 100. Eddy current array probe 100 includes a plurality of probe coils 128 (also referred to herein as an array of coils), for example, probe coils 130, 132, 134, 136, 138, 140, 142, and 144. In the exemplary embodiment, eddy current array probe 100 includes eight probe coils. Alternatively, probe 100 may include any number of probe coils that enables probe 100 to function as described herein. The plurality of probe coils 128 are mounted within tip portion 110 to form an array 128 of coils. Each coil in the array 128 is formed with a substantially cylindrical outer surface 146 such that at least a portion of each coil within the array 128 is positioned adjacent to outer tip 114. In the exemplary embodiment, probe coils 130, 132, 134, 136, 138, 140, 142, and 144 are pairs of side mount coils that are electrically coupled together in series. When activated, probe coil pairs 130, 132, 134, 136, 138, 140, 142, and 144 each generate a magnetic field that is substantially perpendicular to a surface of the component being scanned More specifically, each of probe coil pairs 130, 132, 134, 136, 138, 140, 142, and 144 transmits a transient electromagnetic flux into the component being tested.

Figure 10:
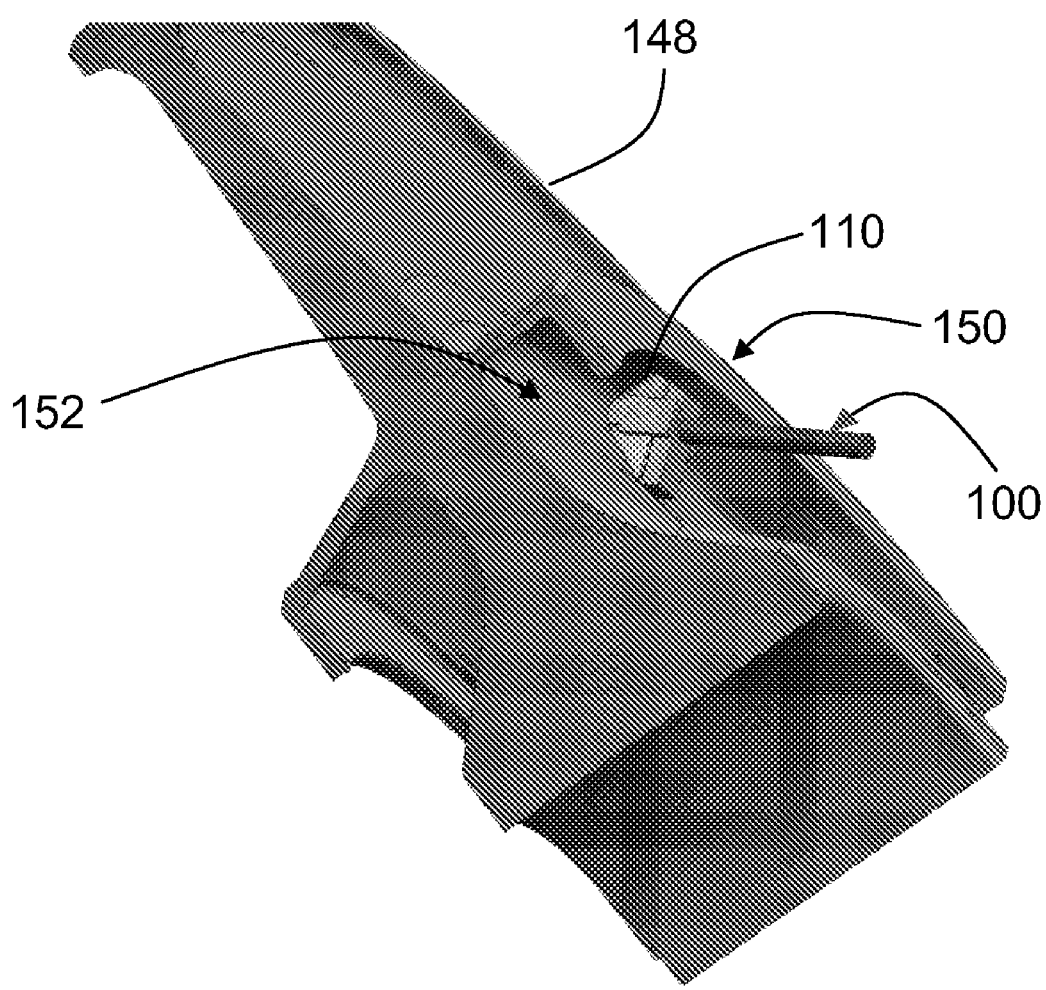
FIG. 10 is a partial perspective view of the eddy current array probe shown in FIG. 6 being used to inspect a component.

FIG. 10 is a partial cut-away view of eddy current array probe 100 and a component 148. Tip portion 110 is a compressible assembly that substantially conforms to the surface 152 of the component 148 being tested when pressure is applied to probe 100. As the contour of surface 152 changes, tip portion 110 is able to flex and adapt to the contour changes. More specifically, because of the orientation of probe coils 130, 132, 134, 136, 138, 140, 142, and 144 (shown in FIG. 9) within array 128 (shown in FIG. 9), as the severity of the contour of surface 152 changes, the plurality of probe coils 130, 132, 134, 136, 138, 140, 142, and 144 remain in contact with the surface 152. In the exemplary embodiment, tip portion 110 is initially configured to substantially conform to the contour of a portion 150 of the surface 152 of the component 148 being tested. Initially substantially conforming to a portion 150 of surface 152 reduces the amount the tip portion 110 has to adapt to remain in contact with surface 152 as the contour of surface 152 changes.

Eddy current array probe 100 is able to substantially conform to a surface of a component that curves in two dimensions. An exemplary embodiment of a component having surfaces that curve in two dimensions is a cylinder. In one dimension, a cylinder is substantially linear. In the other two dimensions, a cylinder includes a radial curvature. An EC array probe that flexes or is formed to conform to the radial curvature may be used to inspect the cylinder.

In contrast to a cylinder, a component may have surfaces that are contoured in three dimensions and that do not include a substantially linear axis. An example of such a component is a fan blisk. A fan blisk may be inspected by a single EC probe. However, to inspect a fan blisk with an EC array probe that inspects a larger area than a single EC probe, an EC array probe that flexes in three dimensions such as, for example, eddy current array probe 100, is necessary.

Figure 11:
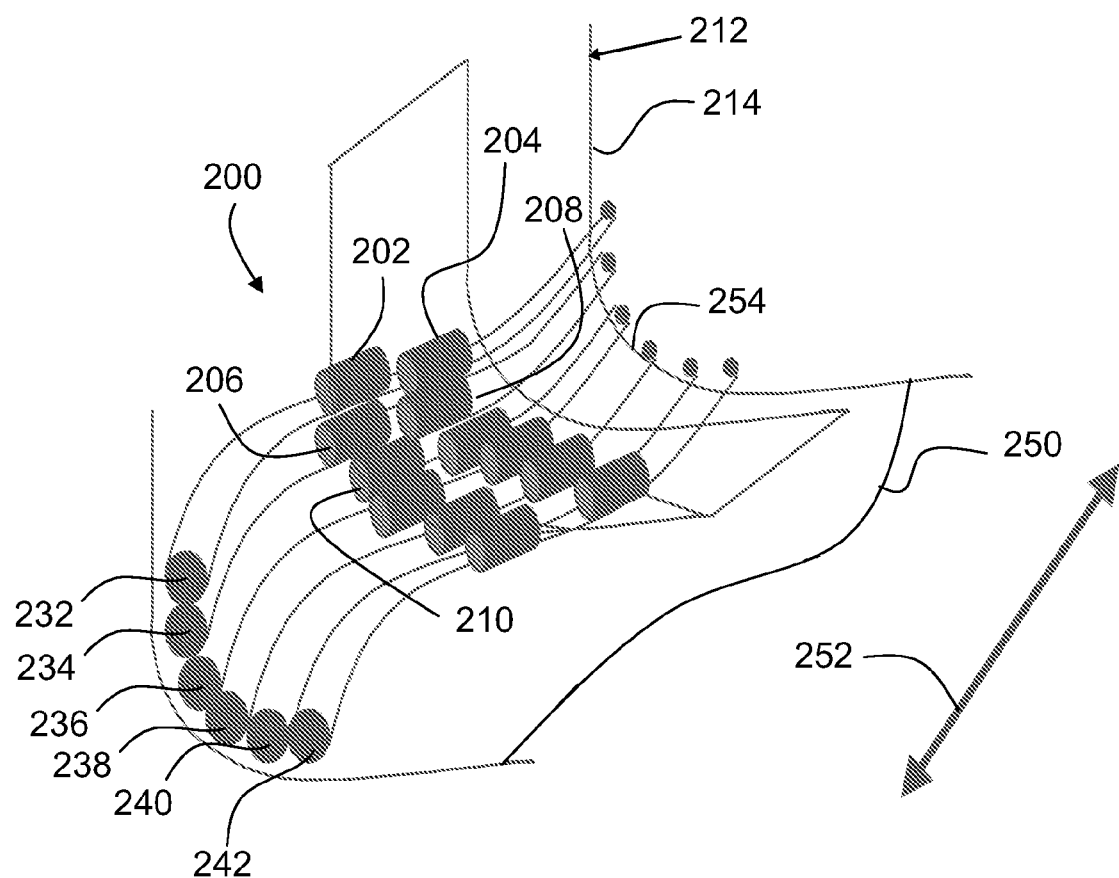
FIG. 11 is a schematic view of a plurality of coils and a component surface.

FIG. 11 is a schematic view of an exemplary plurality of coils 200, for example, coils 202, 204, 206, 208, and 210, and a component 212 having a contoured surface 214. The plurality of coils 200 may be positioned on a tip portion of an EC array probe, for example, tip portion 110 (shown in FIG. 9). In the exemplary embodiment, the plurality of coils 200 are wound about flexible fibers 232, 234, 236, 238, 240, and 242. The flexible fibers enable the plurality of coils 200 to maintain a substantially uniform contact against the contoured surface 214 as the plurality of coils 200 are moved across contoured surface 214 in a scan direction 252.

Figure 12:
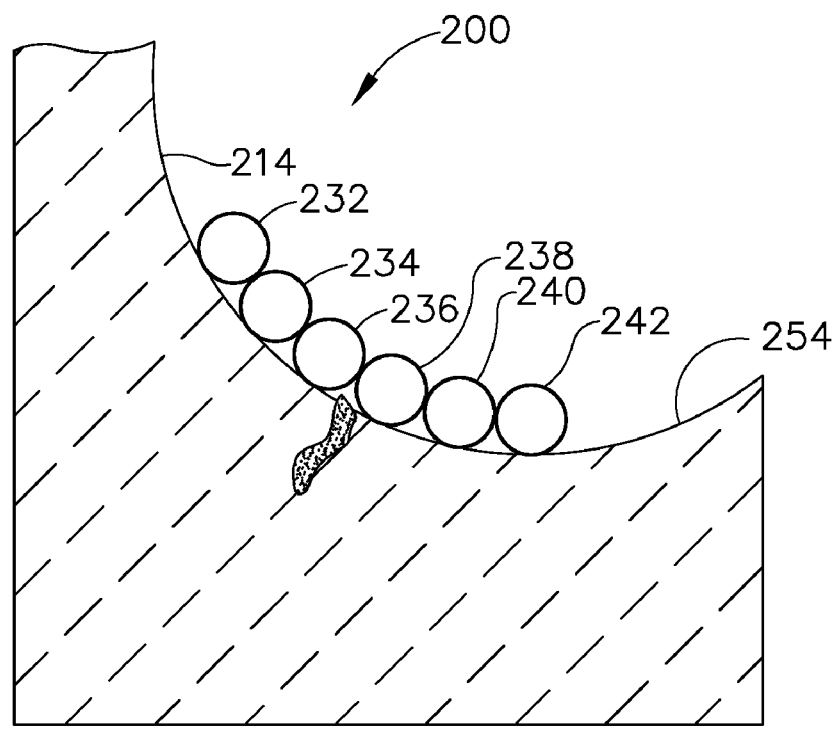
FIG. 12 is a cross-sectional schematic view of a plurality of flexible fibers and a component surface.
Figure 12A:
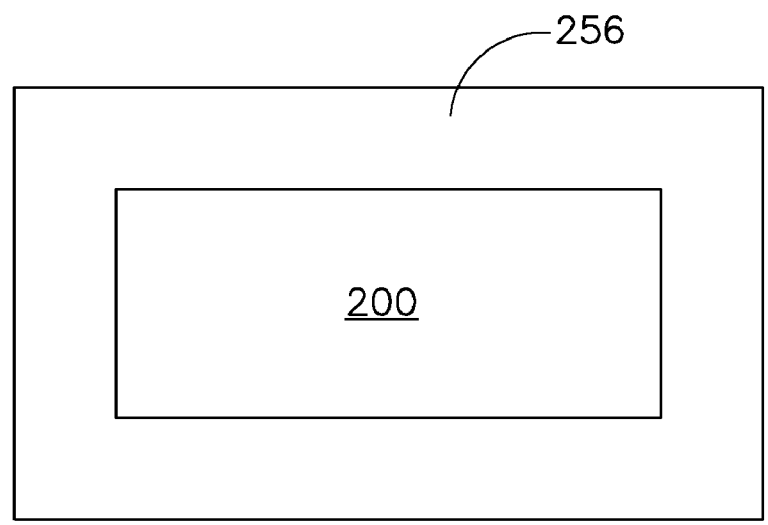
FIG. 12A is a cross-sectional schematic view of a plurality of coils printed on a film and a component surface.

FIG. 12 is a cross-sectional view of an exemplary plurality of flexible fibers 232, 234, 236, 238, 240, and 242 and surface 214. Flexible fibers 232, 234, 236, 238, 240, and 242 are rotatable to enable the plurality of coils 200 to maintain a substantially uniform contact against a plurality of different contours, such as illustrated at 250 and/or 254 of surface 214 (each shown in FIG. 11) as the plurality of coils 200 are moved across surface 214.

Figure 2:
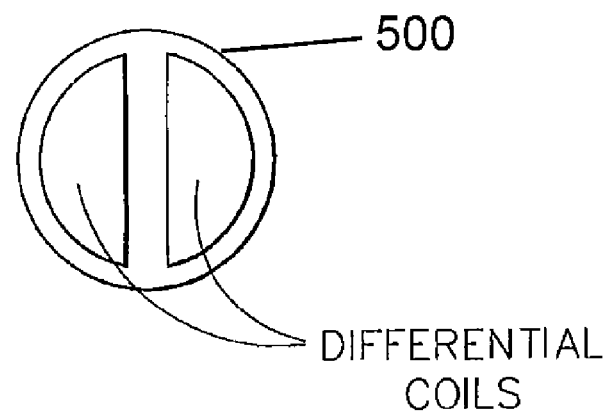
FIG. 2 is a top view of the eddy current probe shown in FIG. 1.
Figure 3:
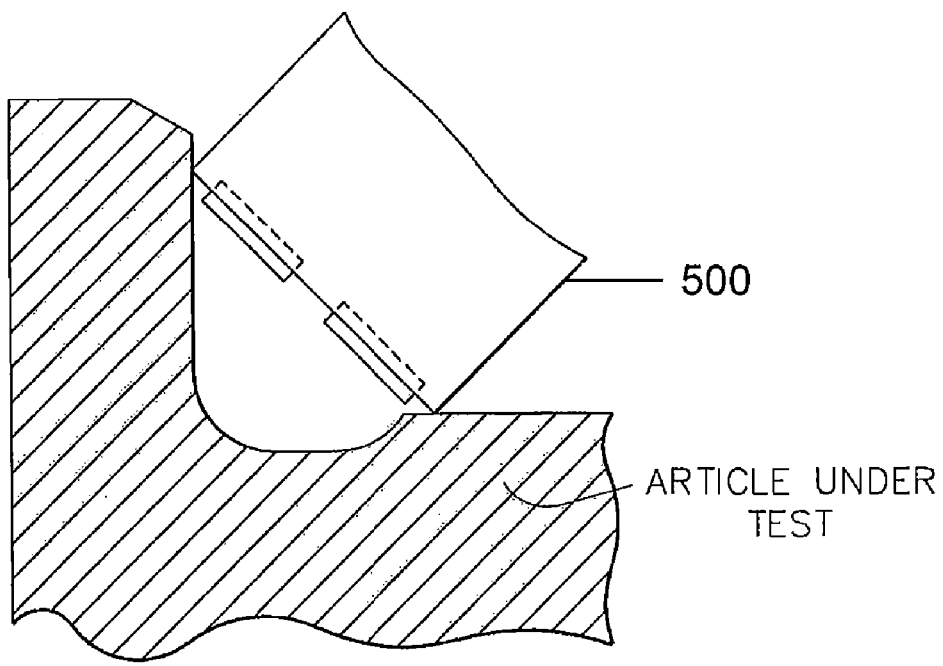
FIG. 3 is a front view of the eddy current probe shown in FIG. 1 illustrating a lift-off effect in an indexing direction.
Figure 4:
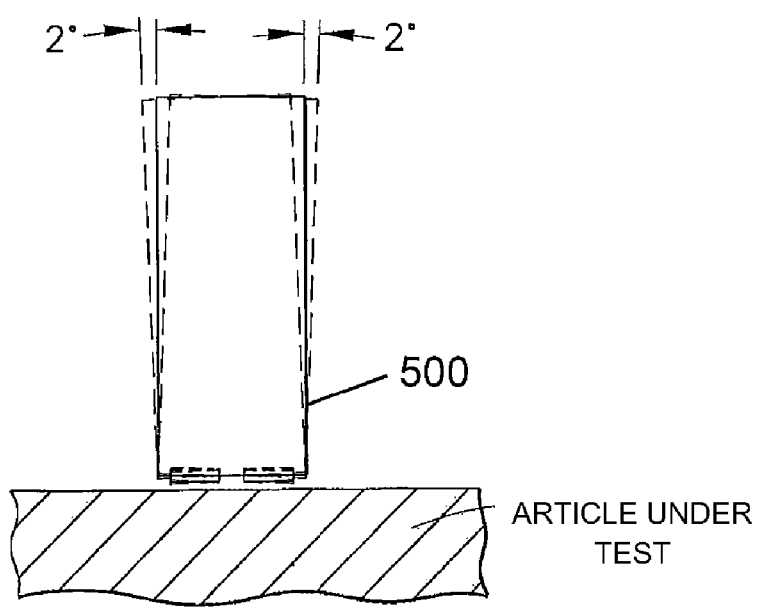
FIG. 4 is a front view of the eddy current probe shown in FIG. 1 and illustrating a lift-off effect in a scan direction.

Unlike known differential probes that may generally be oriented at an angle of no more than approximately 2° (shown in FIG. 2) before the eddy current signal deteriorates, since the plurality of coils 200 are side mount coils, each coil, for example, coils 202, 204, 206, 208, and 210, may be oriented at an angle that is up to approximately 45° to the surface 214 of the component 212 being tested without compromising the EC signal. In other words, while known coils must generally only be oriented normal to the surface being tested to provide accurate results, differential side mount coils are relatively immune to the surface normal requirement. Moreover, the favorable tilt tolerance of side mount coils 200 facilitates the inspection of components having sharp indexing requirements and/or highly contoured surfaces, while using an eddy current array probe.

In another exemplary embodiment, rather than winding the plurality of coils 200 about flexible fibers, the plurality of side mount coils 200 are printed on a flexible film 256. For example, in one embodiment, flexible film 256 is a polyimide film, such as KAPTON® polyimide film, which is commercially available from DUPONT™ of Wilmington, Delaware.

Figure 13:
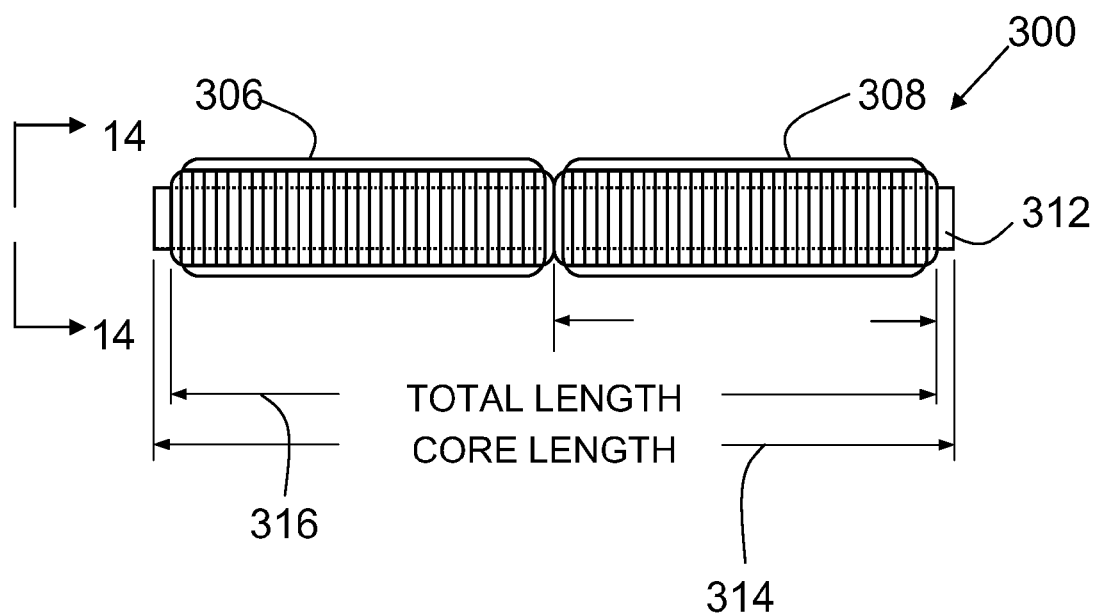
FIG. 13 is a side schematic view of an exemplary differential side mount coil.
Figure 14:
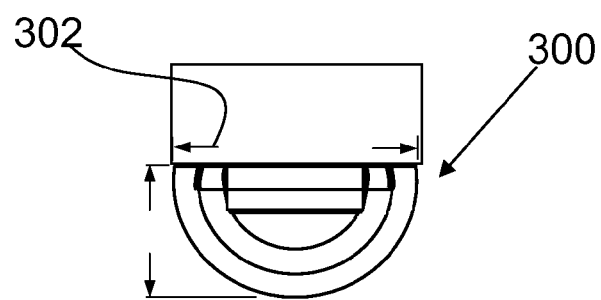
FIG. 14 is a cross-sectional view of the differential side mount coil shown in FIG. 13 and taken along line 14-14.

FIG. 13 is a cross-sectional view of an alternative embodiment of a differential side mount coil 300. FIG. 14 is a side view of differential side mount coil 300. Differential side mount coil 300 is an example of a side mount coil that may be included in the plurality of coils 200 (shown in FIG. 11). In the exemplary embodiment, differential side mount coil 300 has a diameter 302 of approximately 0.032 inches. Differential side mount coil 300 includes two serially coupled coils 306 and 308. Coils 306 and 308 are each approximately 0.037 inches long and coil 300 is approximately 0.075 inches long. Differential side mount coil 300 includes a core 312. In an exemplary embodiment, core 312 is a ferrite core. In another embodiment, core 312 is an air core. In an exemplary embodiment, core 312 has a length 314 that is longer than a length 316 of coils 306 and 308. More specifically, in the exemplary embodiment, core length 314 is approximately 0.080 inches. Moreover, in the exemplary embodiment, differential coils 306 and 308 are shielded. In another exemplary embodiment, differential coils 306 and 308 are unshielded.

Figure 15:
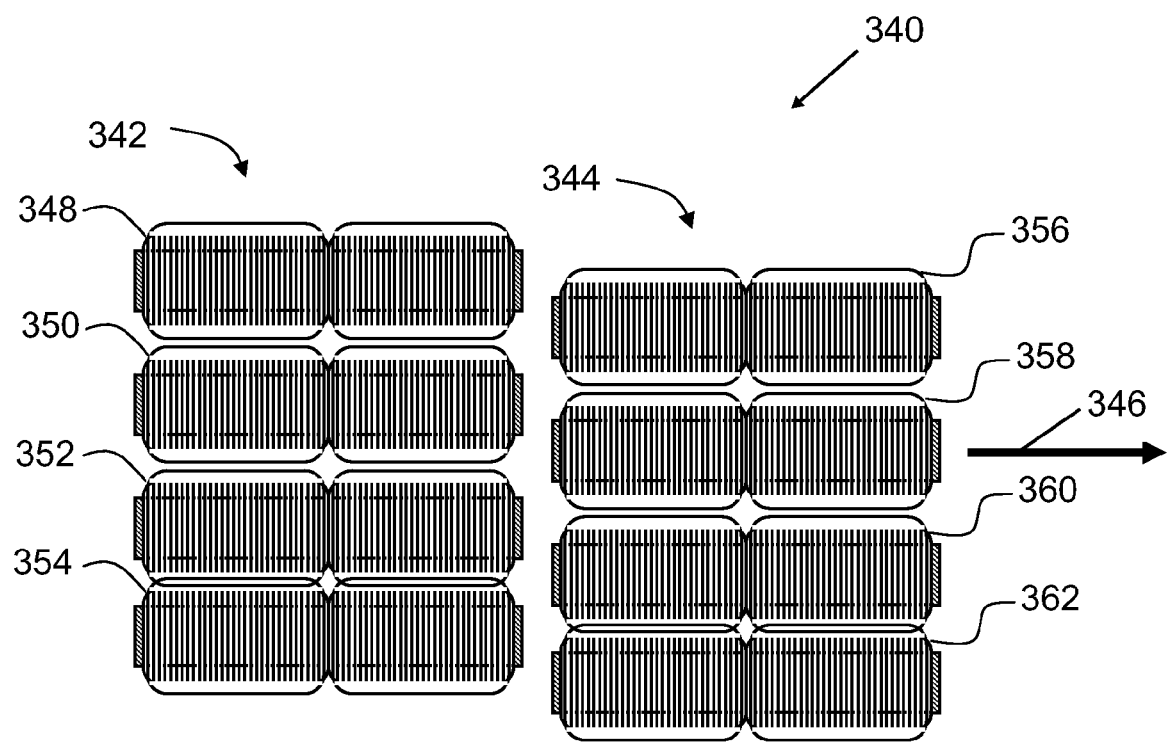
FIG. 15 is a top view of an exemplary array of differential side mount coils.

FIG. 15 is a top view of an array of coils 340. In one embodiment, the array of coils 340 is included within tip portion 110 (shown in FIG. 9). In the exemplary embodiment, array of coils 340 includes a first set of differential coils 342 and a second set of differential coils 344. Each differential coil 348, 350, 352, and 354 within first set of differential coils 342 is not aligned with a corresponding differential coil 356, 358, 360, and 362 within the second set of differential coil 344. Rather, first set of differential coils 342 is offset with respect to the second set of differential coils 344. Offsetting the two sets of differential coils 342 and 344 facilitates ensuring a full coverage of the component 212 (shown in FIG. 11) being tested as array of coils 340 is moved across the surface 214 (shown in FIG. 11) in a scan direction 346.

Figure 16:
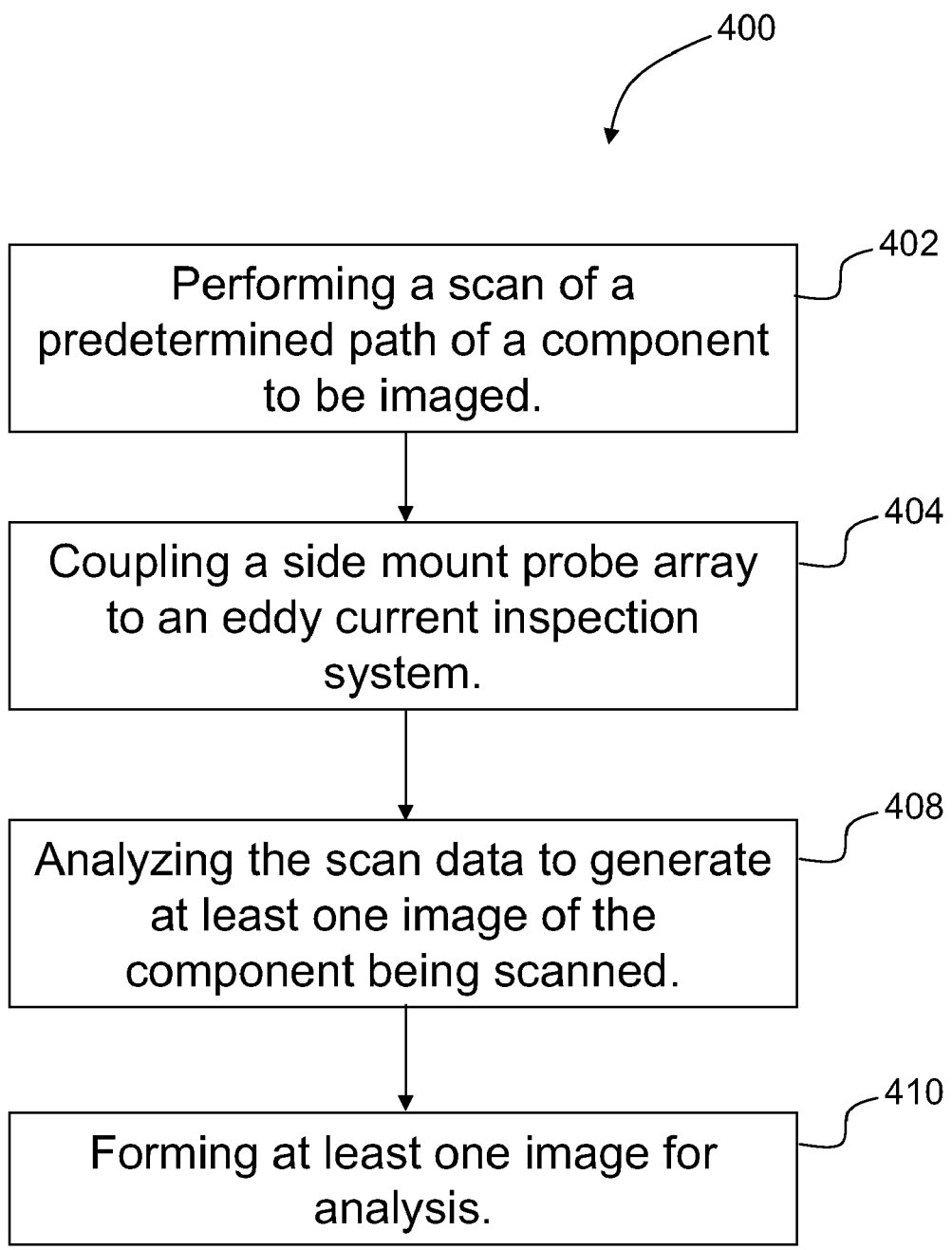
FIG. 16 is a flow chart illustrating an exemplary method of operating eddy current surface flaw detection system and an eddy current array probe.

FIG. 16 is a flow chart illustrating an exemplary method 400 of operating an eddy current surface flaw detection system, such as system 50 (shown in FIG. 6), and using an eddy current array probe, such as probe 100 (shown in FIG. 8). The method 400 includes performing 402 a scan of a predetermined path of a component to be imaged, coupling 404 a side mount array probe, such as array probe 100, to an eddy current inspection system, such as inspection system 50, and analyzing 408 the scan data to generate at least one image of the component being scanned.

Performing 402 a scan of a predetermined path includes directing the eddy current array probe to scan an inspection area. In an exemplary embodiment, Computer Numeric Control (CNC) commands direct the array probe to move along a predetermined path in a scan direction (such as is illustrated in FIG. 11), while acquiring signals from the eddy current array probe. Whereas a single EC probe scans a single line of an inspection area as it moves along a predetermined path, an array probe, such as probe 100, scans a plurality of lines of an inspection area as it moves along a predetermined path.

In the exemplary embodiment, eddy current array probe 100 facilitates maintaining contact with the surface of the component being inspected without unwanted lift-off, even when inspecting a highly contoured outer surface, especially those surfaces having contours in three dimensions. Unlike known eddy current probes, scanning using array probe 100 does not require compensating for expected occurrences of probe lift-off. Also, the amount of time required to scan an outer surface having contours in three dimensions is reduced by using array probe 100 rather than a single eddy current probe, while also achieving inspection coverage and sensitivity requirements for the tested component.

Performing a scan utilizing eddy current array probe 100 facilitates reducing the time and complexity required to scan a curved portion of a component since eddy current array probe 100 is capable of flexing in a first direction to maintain coupling with a surface to be tested while flexing in a second direction perpendicular to the first direction approximately +/−45° with respect to an absolute normal orientation with respect to the component surface without compromising the eddy current signal. Moreover, performing a scan utilizing eddy current array probe 100 facilitates a more robust inspection process that is relatively insensitive to probe-to-probe or machine-to-machine variances that may be common with inspection processes performed using known eddy current probes.

In operation, coupling 404 a side mount probe, such as array probe 100, to an eddy current inspection system includes coupling the eddy current array probe 100 to a probe holder, such as probe manipulator 72 (shown in FIG. 6). A rotation axis is then set to zero degrees before the scan starts. The component is then scanned using the eddy current array probe 100 to generate scan data. Specifically, eddy current inspection system 50 is activated such that the component is scanned in the scanning direction by turning the rotary axis while the probe stays at a relatively fixed position. Eddy current array probe 100 is then moved over any interrupted gaps on the component until the scan is completed in the scanning direction. Unlike a scan using a known probe wherein data collected from multiple rotations of the component must be combined to form an image, because eddy current array probe 100 scans a plurality of lines of an inspection area as it moves along a predetermined path, the image may be formed from data collected during a single rotation of the component.

Analyzing 408 the scan data to generate at least one image of the component being scanned includes collecting the signals, i.e. scan data, transmitted from eddy current array probe 100 and forming 410 at least one image for analysis.

The methods and apparatus described herein facilitate enabling collection of signals from an array of coils configured to inspect a surface that may include curves in three dimensions, thereby minimizing the amount of time needed to acquire and process data compared to known eddy current inspection systems, without having any adverse affects on the sensitivity of the inspection.

The above-described methods and apparatus provide cost-effective and reliable means to facilitate reducing the amount of time needed to perform an eddy current inspection on a component under test. Specifically, the methods and apparatus described herein facilitate reducing an inspection time and improve an eddy current system performance by utilizing an array probe that is able to conform to a surface that curves in three dimensions. The eddy current array probe described herein includes side mount differential coils that are less sensitive to orientation than known eddy current probes, and can be therefore maintain consistent image quality, ensuring sensitivity.

Exemplary embodiments of eddy current inspection systems are described above in detail. The systems are not limited to the specific embodiments described herein, but rather, components of each system may be utilized independently and separately from other components described herein. Each system component can also be used in combination with other system components. More specifically, although the methods and apparatus herein are described with respect to aircraft engine parts, it should be appreciated that the methods and apparatus can also be applied to a wide variety of components used within a steam turbine, a nuclear power plant, an automotive engine, or to inspect any mechanical component.

While the invention has been described in terms of various specific embodiments, those skilled in the art will recognize that the invention can be practiced with modification within the spirit and scope of the claims.

What is claimed is:

1. A method of assembling an eddy current array probe to facilitate nondestructive testing of a sample, said method comprises:
   winding a plurality of differential side mount coils about flexible fibers such that each of the differential side mount coils encircles a flexible fiber;
   coupling the plurality of differential side mount coils and flexible fibers to a compressible tip portion of the eddy current array probe, such that the compressible tip portion has a contour that substantially conforms to a portion of a surface of the sample to be tested.

2. A method according to claim 1 wherein coupling the plurality of differential side mount coils and flexible fibers further comprises coupling the plurality of differential side mount coils to the compressible tip portion which flexes to conform to a surface of a sample having contours in three dimensions.

3. A method according to claim 1 wherein coupling the plurality of differential side mount coils and flexible fibers further comprises positioning a first side mount coil of the plurality of side mount coils substantially parallel to a second side mount coil of the plurality of side mount coils.

4. An eddy current testing device comprising:
   an eddy current array probe comprising a tip portion; and
   a plurality of differential side mount coils positioned at least partially within said tip portion of said eddy current array probe, said plurality of differential side mount coils flexibly coupled together to form an array of coils wherein said plurality of differential side mount coils are wound about one or more flexible fibers such that each of the differential side mount coils encircles a flexible fiber, wherein at least two coils of the plurality of differential side mount coils are wound about a same flexible fiber, the at least two coils spaced along the same flexible fiber, the at least two coils of the plurality of differential side mount coils flexibly coupled together using the same flexible fiber.

5. An eddy current testing device according to claim 4 wherein said tip portion is contoured with a shape that substantially conforms to a portion of a surface of a component being tested, wherein the surface is curved in three dimensions.

6. An eddy current testing device according to claim 4 wherein said tip portion is configured to substantially conform to a changing contour of a surface of a component being tested when said tip portion is forced against the component surface.

7. An eddy current testing device according to claim 4 wherein said plurality of differential side mount coils are oriented in said array of coils within a first row and a second row, said first row of said plurality of differential side mount coils is substantially parallel to said second row of said plurality of differential side mount coils.

8. A surface flaw detection system to facilitate nondestructive inspection of a component, said system comprising:
   a control system; and
   at least one eddy current array probe communicatively coupled to said control system, said eddy current array probe comprising:
   a compressible assembly coupled to said eddy current array probe, said compressible assembly configured to substantially conform to a portion of a surface being tested when forced against the portion of the surface being tested; and
   a plurality of differential side mount coils wound about one or more flexible fibers, such that each of the differential side mount coils encircles a flexible fiber, and oriented in an array at least two coils of said plurality of coils wound about a same flexible fiber, said at least two coils spaced along the same flexible fiber, said at least two coils flexibly coupled together using the same flexible fiber.

9. A surface flaw detection system according to claim 8 wherein the portion of the surface being tested is contoured in three dimensions.

10. A surface flaw detection system according to claim 8 wherein said control system comprises a computer.

11. A surface flaw detection system according to claim 8 wherein said plurality of differential side mount coils comprise a first row of coils and a second row of coils, said first row of coils is oriented substantially parallel to said second row of coils.

\* \* \* \* \*